United States Patent
Opsal et al.

(10) Patent No.: US 7,212,288 B2
(45) Date of Patent: May 1, 2007

(54) POSITION MODULATED OPTICAL REFLECTANCE MEASUREMENT SYSTEM FOR SEMICONDUCTOR METROLOGY

(75) Inventors: Jon Opsal, Livermore, CA (US); Lena Nicolaides, Castro Valley, CA (US); Alex Salnik, Castro Valley, CA (US)

(73) Assignee: Therma-Wave, Inc., Fremont, CA (US)

( * ) Notice: Subject to any disclaimer, the term of this patent is extended or adjusted under 35 U.S.C. 154(b) by 352 days.

(21) Appl. No.: 10/886,110

(22) Filed: Jul. 7, 2004

(65) Prior Publication Data
US 2005/0036136 A1    Feb. 17, 2005

Related U.S. Application Data
(60) Provisional application No. 60/495,195, filed on Aug. 14, 2003.

(51) Int. Cl.
*G01N 21/55* (2006.01)
(52) U.S. Cl. ..................... 356/432; 356/445
(58) Field of Classification Search ............... 356/432, 356/445, 447, 448
See application file for complete search history.

(56) References Cited

U.S. PATENT DOCUMENTS

| | | | |
|---|---|---|---|
| 4,634,290 A | 1/1987 | Rosencwaig et al. | 374/5 |
| 4,636,088 A | 1/1987 | Rosencwaig et al. | 374/5 |
| 4,652,757 A * | 3/1987 | Carver | 356/432 |
| 4,854,710 A | 8/1989 | Opsal et al. | 356/432 |
| 5,074,669 A | 12/1991 | Opsal | 356/445 |
| 5,206,710 A | 4/1993 | Geiler et al. | 356/432 |
| 5,228,776 A * | 7/1993 | Smith et al. | 374/5 |
| 5,408,327 A | 4/1995 | Geiler et al. | 356/432 |
| 5,978,074 A | 11/1999 | Opsal et al. | 356/72 |
| 6,535,285 B1 | 3/2003 | Opsal et al. | 356/369 |
| 2003/0234933 A1 | 12/2003 | Nicolaides et al. | 356/445 |

* cited by examiner

*Primary Examiner*—Richard A. Rosenberger
(74) *Attorney, Agent, or Firm*—Stallman & Pollock LLP

(57) ABSTRACT

A system for evaluating semiconductor wafers includes illumination sources for generating probe and pump beams. The pump beam is focused on the surface of a sample and a beam steering mechanism is used to modulate the point of focus in a predetermined pattern. The moving pump beam introduces thermal and plasma waves in the sample causing changes in the reflectivity of the surface of the sample. The probe beam is focused within or adjacent to the area illuminated by the pump beam. The reflected probe beam is gathered and used to measure the changes in reflectivity induced by the pump beam. By analyzing changes in reflectivity, a processor is able to deduce structure and chemical details of the sample.

21 Claims, 3 Drawing Sheets

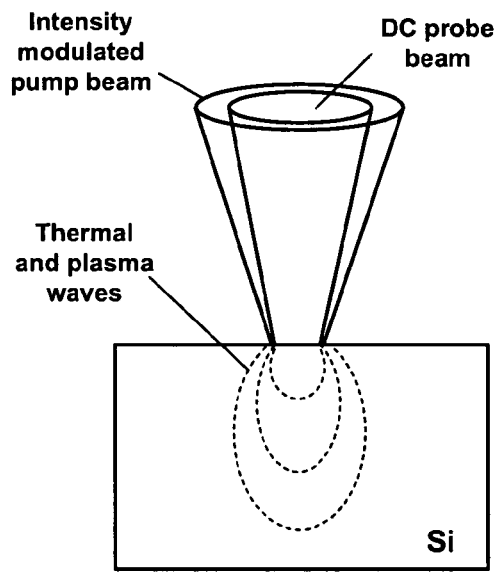
**Fig. 1
(prior art)**
**Fig. 2
(prior art)**
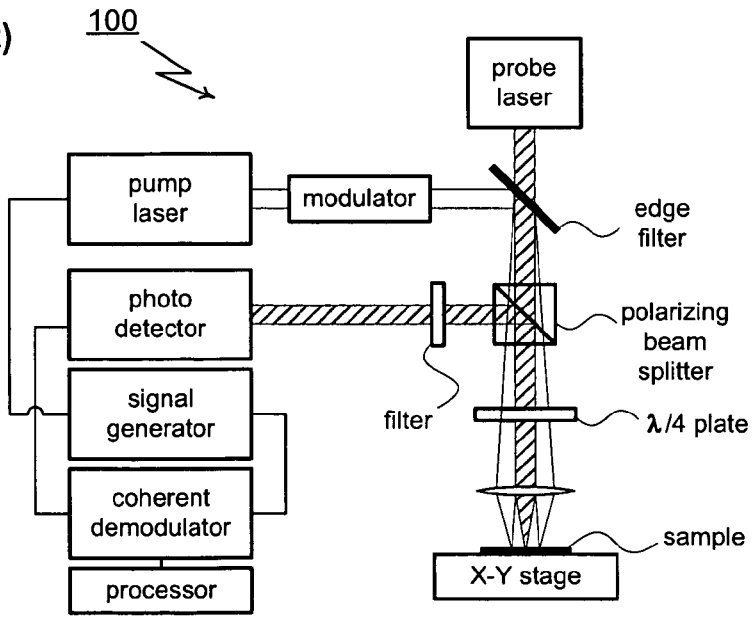

POSITION MODULATED OPTICAL REFLECTANCE MEASUREMENT SYSTEM FOR SEMICONDUCTOR METROLOGY

PRIORITY CLAIM

The present application claims priority to U.S. Provisional Patent Application Ser. No. 60/495,195, filed Aug. 14, 2003, the disclosure of which is incorporated in this document by reference.

TECHNICAL FIELD

The subject invention relates generally to optical methods for inspecting and analyzing semiconductor wafers and other samples. In particular, the subject invention relates to methods for characterizing the effectiveness of implantation and annealing processes for samples both with and without ultra-shallow junctions.

BACKGROUND OF THE INVENTION

Ion implantation and annealing are two processes used during the fabrication of integrated circuits. Ion implantation introduces charged atoms (ions) into the surface region of a semiconductor wafer. Annealing removes damage (changes to the crystalline lattice) that occurs as a side effect of the implantation process. The annealing process also activates implanted ions and changes the type of electrical conductivity of the uppermost layer of a semiconductor. To be effective, the implantation process must produce a layer of implanted ions at the correct depth and concentration. The annealing process must be uniform over the entire surface of the implanted wafer. Correctly controlling these two processes may be difficult, especially in the ultra-shallow junction case, where the implanted layer is very thin and highly doped.

There is a great need in the semiconductor industry for sensitive metrology equipment that can provide high resolution and noncontact evaluation of product Si wafers as they pass through the implantation and annealing fabrication stages. In recent years, a number of products have been developed for the nondestructive evaluation of semiconductor materials. One such product has been successfully marketed by assignee herein under the trademark Therma-Probe (TP). This system incorporates technology described in U.S. Pat. Nos. 4,634,290; 4,636,088; 4,854,710; 5,074,669 and 5,978,074 (each incorporated in this document by reference).

In the basic device described in the patents just cited, an intensity modulated pump laser having a wavelength from the visible part of the spectrum is focused on the sample surface for exciting the sample. In the case of a semiconductor, thermal and carrier plasma waves are generated close to the sample surface which spread out from the pump beam spot inside the sample.

The presence of the thermal and carrier plasma waves affects the reflectivity R at the surface of a semiconductor. Features and regions below the sample surface, such as an implanted region or an ultra-shallow junction alter the propagation of the thermal and carrier plasma waves. In turn, this results in changes in the optical reflectivity at the sample surface. By monitoring the changes in reflectivity, information about characteristics below the surface, such as a degree of damage introduced during the ion implantation process (implantation dose) and/or characteristic depth of the doped region below the sample surface (ultra-shallow junction depth) can be investigated.

In the basic device, a second laser having a visible wavelength different from that of the pump laser is provided for generating a probe beam of radiation. This probe beam is focused collinearly with the pump beam and reflects off the sample surface. A photodetector is provided for monitoring the power of reflected probe beam. This photodetector generates an output signal that is proportional to the reflected power of the probe beam and is therefore indicative of the varying optical reflectivity of the sample surface. A lock-in detector is used to measure both the in-phase (I) and quadrature (Q) components of the signal. The two channels of the output signal, namely the amplitude $A^2=I^2+Q^2$ and phase $\Theta=\tan^{-1}(I/Q)$ are conventionally referred to as the Photomodulated Reflectivity (PMR) or Thermal Wave (TW) signal amplitude and phase, respectively.

Another optical monitoring system based on modulated optical reflectance (MOR) methodology and employing pump-probe beam offset scans is described in U.S. Pat. No. 5,978,074 also incorporated in this document by reference. A block diagram of this photothermal system is shown in FIG. 2. In this system, a tracker mechanism is used to separate the position of the pump and probe beams on the sample surface. TW amplitude and/or phase signals are then measured and analyzed as a function of pump-probe beam separation.

SUMMARY OF THE INVENTION

An embodiment of the present invention includes a method and apparatus for modulated optical reflectance (MOR)-based evaluation of semiconductor samples in which a position modulated pump beam is used in place of conventional intensity-modulated techniques. For a typical implementation, separate lasers generate constant intensity pump and probe beams. A piezo-electrically actuated vibrating mirror is used to induce variations or wobble into the path of the pump beam. The probe beam and the wobbling pump beam are joined and focused (typically using the same objective) on the surface of the sample.

On the sample surface, the position of the probe beam is fixed. The pump beam, on the other hand, moves in a pattern determined by the wobble induced by the vibrating mirror. Typically, this pattern causes the pump beam to scan back and forth along a line that includes the illumination spot of the probe beam. Other patterns of illumination are also possible. The moving pump beam creates a thermal dipole within the sample. The thermal dipole includes thermal and plasma waves within the sample. These waves, in turn induce changes into the reflectivity of the sample surface.

A detector is used to monitor the intensity of the reflected probe beam. A lock-in detector is used to isolate in-phase (I) and quadrature (Q) signals from the probe beam. Properties of the sample are then deduced from the I and/or Q values.

BRIEF DESCRIPTION OF THE DRAWINGS

FIG. 1 is a schematic view describing the operation of prior art MOR-type systems.

FIG. 2 is block diagram of a prior art MOR-type system.

DETAILED DESCRIPTION OF THE PREFERRED EMBODIMENTS

Figure 3:
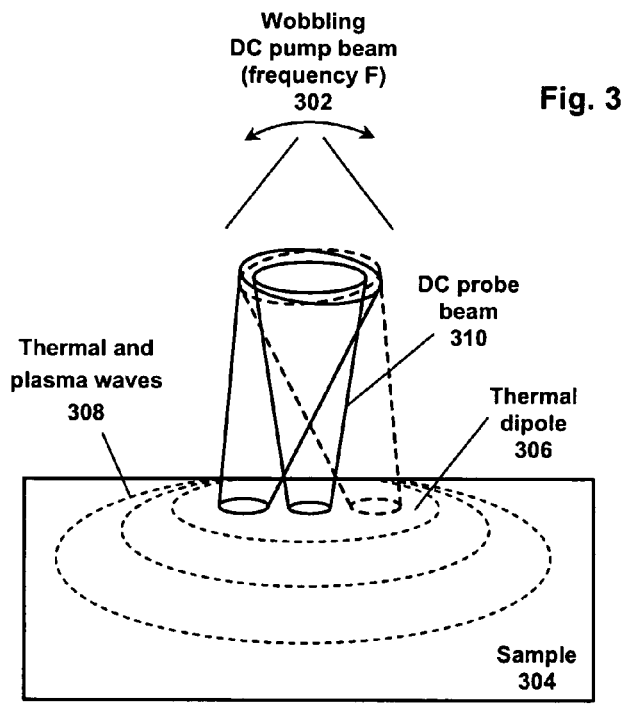
FIG. 3 is a schematic view describing the operation of a MOR-type system using position modulated optical reflectance as provided by an embodiment of the present invention.

An embodiment of the present invention includes a method and apparatus for photo modulated optical response (MOR)-based evaluation of semiconductor samples in which a position modulated pump beam is used in place of conventional intensity-modulated techniques. As shown in FIG. 3, the basic technique uses a DC (constant intensity) pump beam 302 that is focused on the surface of a sample being analyzed 304. The position of the illumination spot produced by the pump beam 302 is modulated or scanned back and forth over the surface of the sample. Optical absorption of the pump irradiation creates a spatially elongated region close to the sample surface that acts as a thermal dipole 306. The lateral dimension of this elongated region may be up to several probe and/or pump beam diameters.

Thermal and plasma waves 308 propagate from the thermal dipole 306 creating region of modulated optical reflectance. Due to a specific geometry of the localized heat source on the semiconductor surface, thermal and plasma waves will have a much larger longitudinal component than in the case of conventional MOR techniques. A probe beam 310 is focused within the region of modulated optical reflectance and the reflected probe beam is monitored to detect changes in reflectivity of the sample induced by the position modulated pump beam. Typically, the detection is synchronized with the position modulation of the pump beam. In the preferred embodiment, the modulation or dithering of the pump beam can be performed at a frequency F set between about 1 Khz and 1 Mhz.

Figure 4:
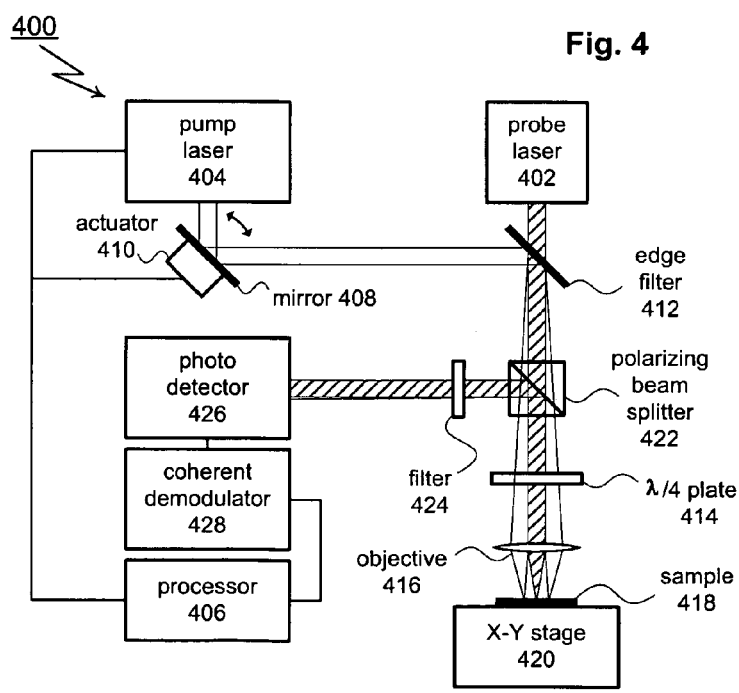
FIG. 4 is block diagram of a MOR-type system using position modulated optical reflectance as provided by an embodiment of the present invention.

In FIG. 4, one possible implementation for a position modulated reflectance measurement system is shown and generally designated 400. As shown, modulated reflectance measurement system 400 includes a probe laser 402 that creates an output known as the probe beam. The probe beam is typically in the visible part of the spectrum (500 to 800 nm) but other wavelength may also be used. For some implementations, the probe laser 402 may be tunable to control the spectral content of the probe beam. System 400 also includes a pump laser 404 with an output (known as the pump beam) that is typically in the visible part of the spectrum but may also be in the UV to near-UV spectral range (420 to 420 nm). Pump laser 404 typically operates at a constant intensity. There may be cases, however where it is desirable to modulate the intensity of the pump beam. This can be accomplished by controlling pump laser 404 or by using a modulator placed in the path of the pump beam (modulator not shown). Lasers 402, 404 are generally diode-based or diode-pumped semiconductor lasers and are controlled by a processor 406.

The pump beam output of pump laser 404 is directed by a mirror 408. Mirror 408 pivots in the direction of the curved arrow (shown adjacent to mirror 408) under control of an actuator 410. Actuator is typically of the piezo-electric type and is controlled by processor 406. This allows processor 406 to alter the path of the pump beam. It should be noted that the use of actuator 410 and mirror 408 are representative and that a wide range of alternative beam steering technologies exist and may be used within measurement system 400.

After leaving mirror 408, the pump beam is joined with the probe beam by an dichroic mirror (edge filter) 412. The combined beams are then conveyed through a quarter-wave plate 414 and objective 416 onto sample 418. Sample 418 is positioned on an X-Y stage 420 allowing sample 418 to be moved in translation relative to the collinear beams.

After striking sample 418, a reflected portion of the probe and pump beams is collected by objective 416 and directed towards a beam splitter 422. Beam splitter 422 redirects the combined beams through a filter 424 and on to a detector 426. Filter 424 removes the probe beam components of the combined beams before they can be received by detector 426. Detector 426 measures the energy reflected by sample 418 and forwards a corresponding signal to a coherent demodulator 428. Coherent demodulator 428 typically includes a lock-in amplifier that uses the drive signal for actuator 410 along with the output of detector 426 to produce quadrature (Q) and in-phase (I) signals for analysis. Processor 406 typically converts the Q and I signals to amplitude and/or phase values to analyze the sample. In other cases, the Q and I signals are used directly.

Figure 5A:
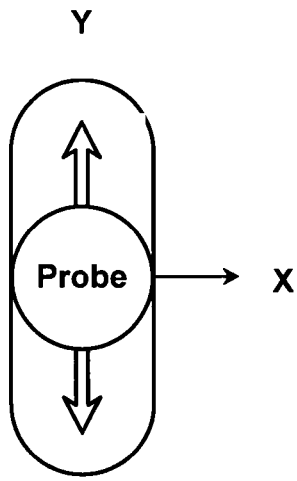
FIG. 5a describes a mode of operation for the system of FIG. 4 in which the pump beam is scanned over the probe beam illumination spot along a line parallel to the X axis.
Figure 5B:
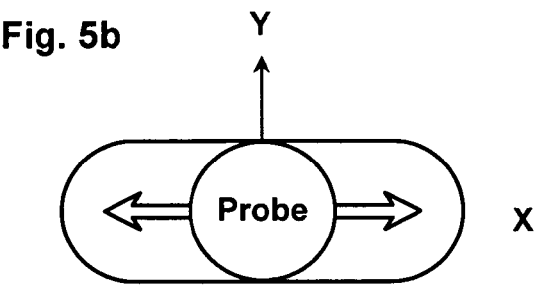
FIG. 5b describes a mode of operation for the system of FIG. 4 in which the pump beam is scanned over the probe beam illumination spot along a line parallel to the Y axis.
Figure 5C:
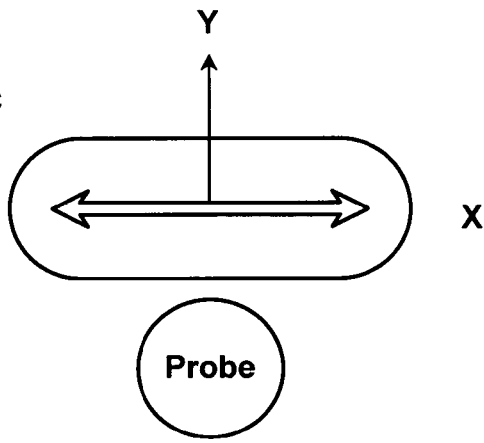
FIG. 5c describes a mode of operation for the system of FIG. 4 in which the pump beam is scanned adjacently to the probe beam illumination spot along a line parallel to the X axis.
Figure 5D:
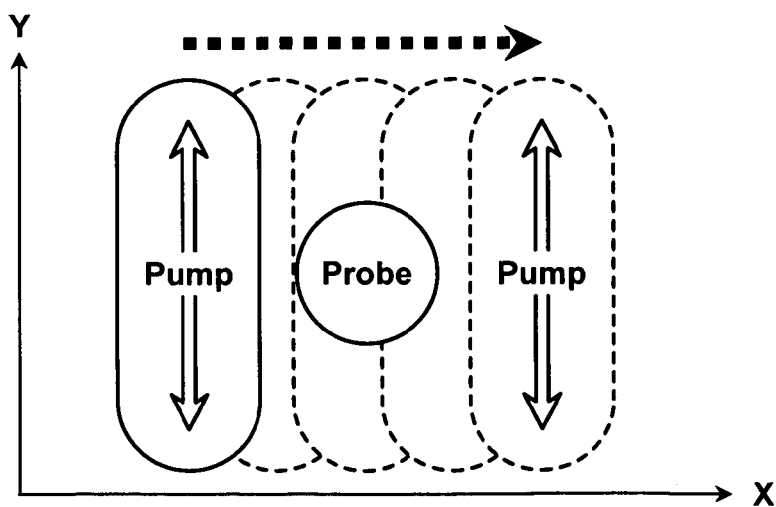
FIG. 5d describes a mode of operation for the system of FIG. 4 in which the pump beam is scanned in both X and Y directions to illuminate an area that includes the probe beam illumination spot.

Actuator 410 and mirror 408 allow the processor 406 to modulate the position of the pump beam on the surface of the sample 418. FIG. 5 illustrates several different ways in which position modulation can be performed. The pump beam can be wobbled either along x or y-axes (FIGS. 5a and 5b, view from the top). In addition to wobbling with the probe beam and pump dipole superimposed, the pump beam dipole can be laterally displaced from the probe beam. This is shown, for example in FIG. 5c. In addition, the pump beam dipole created along the Y axis can be scanned across the position of the probe beam, for example, along an X-axis as shown in FIG. 5d. Data can be taken as a function of the X-position of the pump beam dipole thus performing an operation similar to pump-probe beam offset scan in a prior art system (see FIG. 2).

It should be noted that the methods and apparatus just described are subject to numerous variations. For example, in certain samples, the dipole may also create a periodic physical variation at the surface of the sample similar to the "bump" created with an intensity modulated pump beam. Accordingly, it may also be possible to monitor periodic changes in the position of the reflected probe beam with a split or quad detector. See U.S. Pat. Nos. 4,521,118 and 4,522,510 both incorporated herein by reference.

It should also be noted that many of the variations described in U.S. Pat. No. 5,978,074 could also be applied to this concept. For example, it would be possible to intensity modulate the probe beam and arrange the detector to monitor at a "difference" frequency which would be the difference between the probe beam modulation frequency and the dithering frequency of the pump beam. Further, the dithering frequency does not have to be constant but could be varied (in steps or continuously) to gain further information. In addition, measurements can be taken at different pump and probe beam spot sizes.

It should also be noted that position modulated optical reflectance technology can be implemented and used either alone or in combination with existing MOR (which would include conventional intensity modulation of the pump beam) as well as other metrology schemes (photothermal radiometry, optical methods, X-ray reflection, four-point probe resistivity measurements, etc. See U.S. Pat. Nos. 6,535,285 and 6,583,876 incorporated by reference).

What is claimed is:

1. A method of optically inspecting and evaluating a sample, the method comprising:
   creating a region of modulated optical reflectance within the sample by focusing a pump beam on the sample and subsequently modulating the position of the pump beam on the sample;
   directing a probe beam to be reflected by the region of modulated optical reflectance;
   monitoring the reflected probe beam and generating output signals in response thereto the output signals containing information which can be used to evaluate the sample.

2. A method as recited in claim 1 that further comprises: analyzing the output signals with a phase synchronous detection system and generating in-phase and quadrature signals.

3. A method as recited in claim 1 that further comprises: modulating the intensity of the pump beam.

4. A method as recited in claim 1 in which the probe beam illuminates an area within the area illuminated by the pump beam.

5. A method as recited in claim 1 in which the probe beam illuminates an area adjacent to the area illuminated by the pump beam.

6. A method as recited in claim 1 in which the position of the focal point of the pump beam is modulated at a fixed frequency.

7. A method as recited in claim 1 in which the output signals are analyzed as a function of the separation between pump and probe beams.

8. An apparatus for optically inspecting and evaluating a sample, the apparatus comprising:
   a first illumination source producing a pump beam;
   a second illumination source producing a probe beam;
   illumination side optics configured to project the pump beam to illuminate a spot on the surface of the sample, where the position of the illumination spot is modulated to produce a region of modulated optical reflectance, the illumination side optics also configured to project the probe beam to be reflected by the region of modulated optical reflectance;
   a detector for monitoring the reflected probe beam and generating output signals in response thereto; and
   a processor for evaluating the sample by analyzing the output signals.

9. An apparatus as recited in claim 8 that further comprises: a lock-in amplifier for analyzing the output signals to generate in-phase and quadrature signals.

10. An apparatus as recited in claim 8 that further comprises: something for modulating the intensity of the pump beam.

11. An apparatus as recited in claim 8 in which the collection side optics are configured so that the probe beam illuminates an area within the area illuminated by the pump beam.

12. An apparatus as recited in claim 8 in which the collection side optics are configured so that the probe beam illuminates an area adjacent to the area illuminated by the pump beam.

13. An apparatus as recited in claim 8 in which the position of the illumination spot is modulated at a fixed frequency.

14. An apparatus as recited in claim 8 in which the output signals are analyzed as a function of the separation between pump and probe beams.

15. A system for optically inspecting and evaluating a sample in which a position modulated pump beam is used to create a region of modulated optical reflectance within the sample and a probe beam is used to monitor the reflectance of the region of modulated optical reflectance.

16. A method of evaluating a sample comprising the steps of:
   directing a pump beam to the surface of the sample;
   dithering the position of the pump beam about a center point at a predetermined frequency in order to create modulated variations in the sample which in turn create modulated changes near the surface of the sample
   directing a probe beam to the surface of the sample in the region where the modulated changes have been created;
   monitoring the modulated changes induced in the probe beam by the modulated changes in the sample and generating output signals in response thereto the output signals containing information which can be used to evaluate the sample.

17. A method as recited in claim 16, wherein the modulated power of the reflected probe beam is monitored.

18. A method as recited in claim 16, wherein the modulated changes in position of the probe beam are monitored.

19. An apparatus for evaluating a sample comprising:
   a first light source for generating a pump beam;
   a beam steering mechanism for directing the pump beam to the surface of the sample and dithering the position of the beam on the sample at a modulation frequency in order to create modulated variations in the sample;
   a second light source for generating a probe beam;
   a lens for focusing the probe beam onto the sample in the region where the modulated variations have been created;
   a detector for monitoring the modulated changes induced in the probe beam by the modulated changes in the sample and generating output signals in response thereto; and
   a processor for evaluating the sample based on the output signals.

20. An apparatus as recited in claim 19, wherein the detector monitors the modulated power of the reflected probe beam.

21. An apparatus as recited in claim 20, wherein the processor analyzes the modulated changes in the probe beam that are phase synchronous with the modulation frequency of the dithering of the pump beam.

* * * * *